United States Patent [19]

Ledley

[11] Patent Number: 4,563,173

[45] Date of Patent: Jan. 7, 1986

[54] PUMP-ACTUATED SEQUENCING VALVE AND SYSTEM

[75] Inventor: Robert S. Ledley, Silver Spring, Md.

[73] Assignee: National Biomedical Research Foundation, Washington, D.C.

[21] Appl. No.: 486,600

[22] Filed: Apr. 19, 1983

[51] Int. Cl.$^4$ .............................................. A61M 5/00
[52] U.S. Cl. ..................................... 604/81; 604/247; 604/151; 604/30; 604/284; 604/83; 128/DIG. 12; 128/DIG. 13; 137/565
[58] Field of Search ................... 604/247, 249, 67, 80, 604/81, 151–154, DIG. 12, DIG. 13, 131, 132, 141, 142, 65, 32, 284, 245, 66, 83, 9, 30, 56, 82; 128/DIG. 12, DIG. 13; 137/565

[56] References Cited

U.S. PATENT DOCUMENTS

| | | | |
|---|---|---|---|
| 1,882,314 | 10/1932 | Burt | 137/519.5 |
| 2,699,124 | 1/1955 | Moe | 103/228 |
| 2,999,499 | 9/1961 | Willet | 604/80 |
| 3,648,694 | 3/1972 | Mogos | 128/DIG. 12 |
| 3,800,794 | 4/1974 | Georgi | 128/DIG. 13 |
| 3,886,937 | 6/1975 | Bobo et al. | 128/214 R |
| 3,890,968 | 6/1975 | Pierce et al. | 128/DIG. 13 |
| 4,103,686 | 8/1978 | LeFevre | 128/214 R |
| 4,114,617 | 9/1978 | Turner | 604/80 |
| 4,215,695 | 8/1980 | Spitz et al. | 128/350 R |
| 4,324,238 | 4/1982 | Genese et al. | 604/247 |
| 4,333,454 | 6/1982 | Hargest, III | 604/30 |
| 4,447,224 | 5/1984 | Decant, Jr. et al. | 128/DIG. 13 |
| 4,451,255 | 5/1984 | Bujan et al. | 604/151 |

*Primary Examiner*—C. Fred Rosenbaum
*Assistant Examiner*—Mark D. Rooney
*Attorney, Agent, or Firm*—Joseph G. Seeber

[57] ABSTRACT

A pump-actuated sequencing valve for sequentially administering, to a patient, two fluids contained in separate respective reservoirs, wherein the fluid is pumped from a first one of the two reservoirs by means of a pump associated therewith. The valve comprises a first portion connected to the first reservoir, a second portion connected to the second reservoir, and a third portion connected between the first and second portions, on the one hand, and the patient, on the other hand. The second portion includes a ball valve which is pressure-responsive to operation of the pump for blocking flow of fluid to and from the second reservoir, thus blocking both forward flow from the second reservoir and backflow from the sequencing valve toward the second reservoir. The sequencing valve is, preferably, employed in a pump-actuated sequencing system which includes a further valve disposed between the second reservoir and the second portion, and control means responsive to non-operation/operation of the pump for automatically opening/closing the further valve so as to permit/block flow of fluid from the second reservoir to the sequencing valve.

10 Claims, 4 Drawing Figures

PUMP-ACTUATED SEQUENCING VALVE AND SYSTEM

BACKGROUND OF THE INVENTION

1. Field of the Invention

The present invention relates to a pump-actuated sequencing valve and system for sequentially administering, to a patient, two fluids contained in separate respective reservoirs, the fluid being pumped from one of the two reservoirs by means of a pump associated therewith.

2. Description of Prior Art

In the medical treatment of patients, it is frequently required to sequentially administer, to a patient, two different fluids. For example, in the area of digital fluoroscopy, sequential administration of a contrast media and a saline solution is required.

One technique of the prior art called for the contrast media to be poured into a cylindrical reservoir, followed by careful pouring of the saline solution into the reservoir on top of the contrast media. Since the contrast media is a more dense substance than the saline solution, it was hoped that the contrast media would remain, in an unmixed state, in the bottom portion of the cylinder, such that, when pump pressure was applied from the top of the cylinder, the contrast media would be forced into the intravenous feedline ahead of the saline solution.

The problem with this technique of the prior art was that even the most skilled and experienced person found it difficult to pour the contrast media and saline solution into the cylinder with such care as to prevent any mixing whatsoever of the two solutions. In addition, during the pumping procedure, mixing often occurred. Such mixture of the contrast media and saline solution has obvious harmful effects in terms of obtaining the best possible results from digital fluoroscopy procedures.

Medical administration sets for the dispensation of plural medical liquids from separate reservoirs have been developed. For example, see U.S. Pat. No. 3,886,937—Bobo et al and U.S. Pat. No. 4,324,238—Genese et al. However, these two cited patents are not suitable for the type of sequential administration involving the pumping of a contrast media via an intravenous feedline into a patient, followed by flow of other intravenous solution, such as saline solution, into the patient.

In addition, such arrangements of the prior art often do not preclude the backflow of solution from one reservoir into the feedline connected to the other reservoir.

Other patents generally pertinent to the invention disclosed herein are the following: U.S. Pat. No. 2,699,124—Moe; U.S. Pat. No. 4,103,686—LeFevre; and U.S. Pat. No. 4,215,695—Spitz et al.

SUMMARY OF THE INVENTION

The present invention relates to a pump-actuated sequencing valve and system for sequentially administering, to a patient, two fluids contained in two separate respective reservoirs, wherein the fluid is pumped from a first one of the reservoirs by means of a pump.

More specifically, the pump-actuated sequencing valve of the present invention comprises a first portion connected to a first reservoir, a second portion connected to a second reservoir, and a third portion connected between the first and second portions, on the one hand, and the patient, on the other hand, for conveying fluid to the patient. In accordance with the present invention, the second portion includes a ball valve which is pressure-responsive, and which more particularly is responsive to the pump being placed in the operating condition for blocking the flow of fluid to and from the second reservoir. The ball valve is further responsive to the pump being placed in an inoperative condition for permitting flow of fluid from the second reservoir. In this manner, when the pump is operating (to pump fluid from the first reservoir), backflow of fluid into the second reservoir is precluded.

In accordance with a further feature of the invention, the second portion of the sequencing valve is provided with a restraining mechanism which limits the free movement of the ball valve when the ball valve "floats" during non-operation of the pump associated with the first reservoir.

Finally, in accordance with a further feature of the invention, the pump-actuated sequencing valve is employed in a pump-actuated sequencing system which comprises not only the sequencing valve but also a further valve disposed between the second reservoir and the second portion of the sequencing valve, the further valve being responsive to non-operation of the pump for permitting flow of fluid from the second reservoir to the second portion of the sequencing valve.

Therefore, it is a primary object of the present invention to provide a pump-actuated sequencing valve for sequentially administering, to a patient, two fluids contained in two respective reservoirs.

It is an additional object of the present invention to provide a pump-actuated sequencing valve which employs a ball valve which is pressure-responsive in accordance with the operation or non-operation of a pump associated with one of two reservoirs.

It is an additional object of the present invention to provide a restraining mechanism, in the sequencing valve, for restraining the movement of the ball valve during non-operation of the pump.

It is an additional object of the present invention to provide a pump-actuated sequencing system comprising a further valve responsive to non-operation of a pump associated with one reservoir for permitting flow of fluid from the other reservoir.

With the above and other objects in mind, as will hereinafter appear, the invention will now be more clearly understood by reference to the following detailed description, the accompanying drawings, and the appended claims.

DETAILED DESCRIPTION

The invention will now be described in more detail, with reference to FIG. 1, which is a diagrammatic representation of a pump-actuated sequencing system in which the pump-actuated sequencing valve of the present invention is employed.

Figure 1:
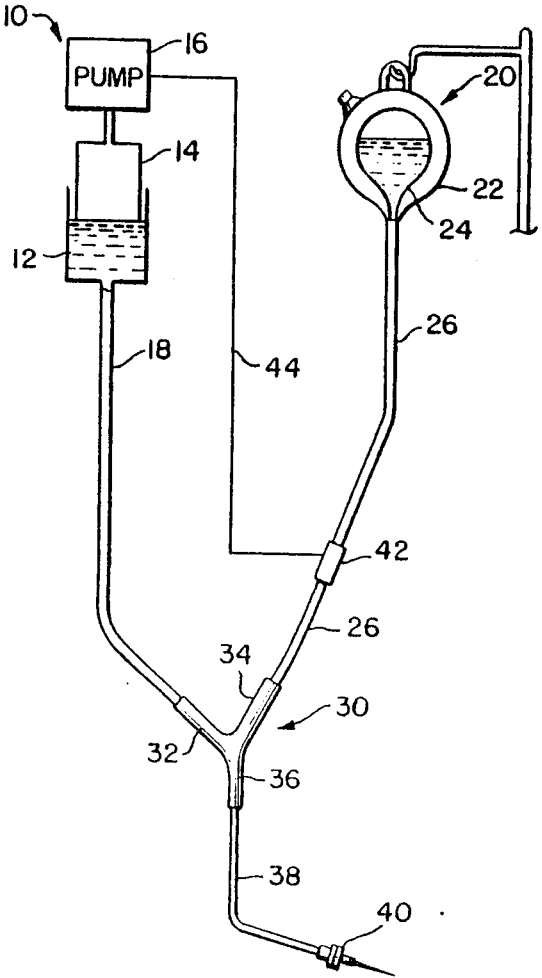
FIG. 1 is a diagrammatic representation of a pump-actuated sequencing system in which the pump-actuated sequencing valve of the present invention is employed.

As seen in FIG. 1, the sequencing system 10 includes a reservoir 12 containing fluid which is forced from the reservoir 12 into a feedline 18 by operation of a cylinder 14 which is driven by a pump 16. The system 10 also includes a further reservoir 20 suspended above the patient at a sufficient height to cause the fluid contained in the reservoir 20 to flow into the feedline 26 associated therewith.

In a particular application of the sequencing system 10, the reservoir 12 contains contrast media, while the reservoir 20 comprises an intravenous bag which typically has dual layers 22 and 24, the inner layer 24 holding a fluid, such as saline solution (in the particular application being discussed), and the space between the outer layer 22 and the inner layer 24 being occupied by compressed air.

The system 10 further comprises a pump-actuated sequencing valve 30, which in turn comprises respective portions 32, 34 and 36, the portion 32 being connected, via the feedline 18, to the reservoir 12, and the portion 34 being connected, via feedline 26, to the reservoir 20. Further portion 36 is connected, via feedline 38, to an intravenous needle 40 inserted into the vein of the patient.

In a preferred embodiment of the invention, a further valve 42 is inserted in the feedline 26, the valve 42 being electrically connected (or otherwise connected, as would be obvious to one skilled in the art) to the pump 16.

In operation, when it is desired to administer sequential solutions (such as contrast media followed by saline solution) to a patient, the pump 16 is turned on, so as to cause expulsion of contrast media from the reservoir 12 under operation of the pump cylinder 14, and contrast media flows through feedline 18, portion 32, portion 36, feedline 38 and needle 40 into the patient. During this stage of operation, moreover, the pressure resulting from pumping of contrast media through the feedline 18, portion 32, portion 36 and feedline 38 causes a valve mechanism (to be discussed in more detail below) contained within portion 34 to close, precluding backflow of contrast media to feedline 26.

After a predetermined time, that is, after flow of a predetermined volume of contrast media into the patient, the pump 16 is stopped, resulting in a decrease in pressure within the sequencing valve 30. Accordingly, the valve mechanism (to be discussed in more detail below) contained within the sequencing valve 30 opens, and intravenous fluid (saline solution) is permitted to flow from reservoir 20, via feedline 26, portions 34 and 36, feedline 38, and needle 40, into the patient.

In accordance with an important feature of the present invention, the pump-actuated sequencing system is provided with a valve 42 located in feedline 26, and electrically (or otherwise) connected to the pump 16. In accordance with the present invention, when the pump is turned on, so as to force contrast media into feedline 18, valve 42 is automatically closed, so as to preclude flow of saline solution from reservoir 20 through feedline 26 into sequencing valve 30. As mentioned above, at the same time, the pressure of flow of contrast media through sequencing valve 30 causes a valve mechanism (to be described below) contained within the sequencing valve 30 to close, thus precluding backflow of contrast media into feedline 26. Conversely, when the pump is turned off, so as to stop the flow of contrast media into feedline 18, valve 42 is automatically opened so as to permit flow of saline solution from reservoir 20 into feedline 26. Automatic closing and opening of valve 42 will be discussed in more detail below, with reference to FIG. 4.

Figure 2:
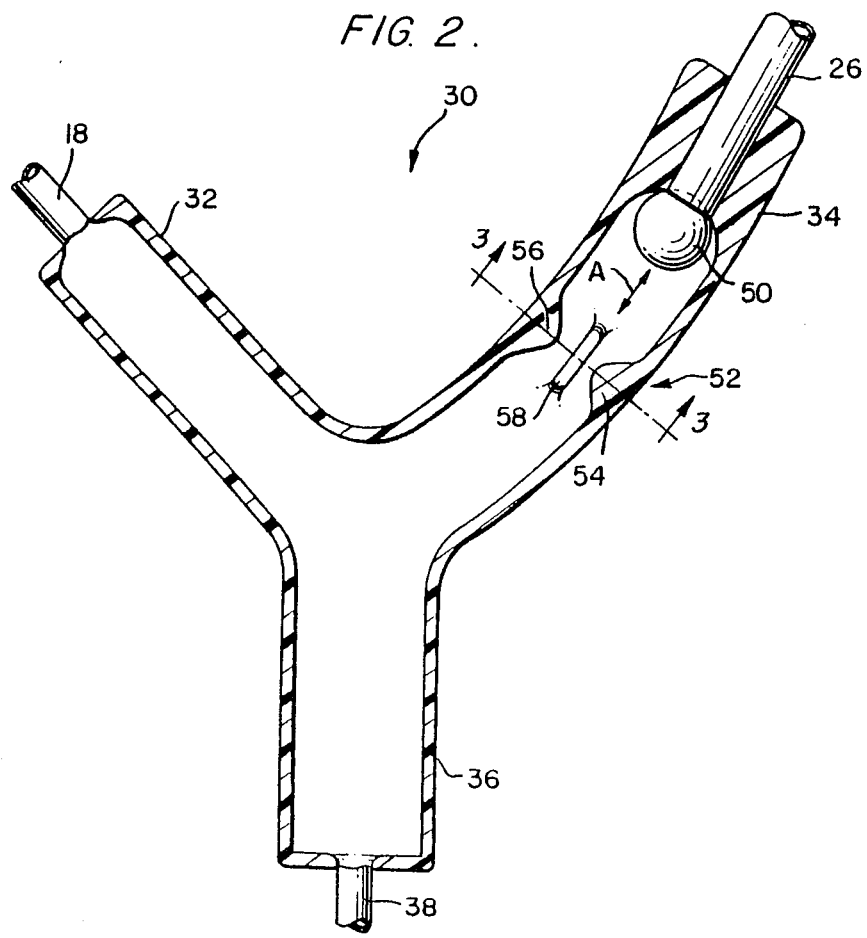
FIG. 2 is a more detailed diagram, in cross-section, of the pump-actuated sequencing valve.

FIG. 2 is a cross-sectional diagram, in more detail, of the pump-actuated sequencing valve 30 of FIG. 1. As seen therein, the valve 30 comprises a first portion 32 connected to feedline 18, a second portion 34 connected to feedline 26, and a third portion 36 connected to feedline 38, as previously discussed with reference to FIG. 1.

More particularly, portion 34 contains a ball valve 50, which is shown in FIG. 2 in its closed position, fitting snugly against the end of feedline 26. As indicated by arrow A in FIG. 2, the ball 50 has room to move or "float" in response to lack of pressure within the sequencing valve 30. That is to say, when the pump 16 (FIG. 1) is activated to pump fluid through feedline 18 and portion 32, the resulting pressure forces the ball valve 50 into a snug fit against the open end of feedline 26, thus precluding backflow of fluid into feedline 26. Conversely, when the pump 16 is non-operational, and there is no fluid passing through feedline 18 into portion 32, there is a resultant lack of pressure in the valve 30, and the ball valve 50 moves downwardly and to the left (in FIG. 2) so as to open the end of feedline 26, thus permitting fluid to flow from reservoir 20 through feedline 26 into the portion 34 of valve 30, and further through the portion 36 and feedline 38 to the needle 40 inserted into the vein of the patient.

Further referring to FIG. 2, specifically to portion 34 of sequencing valve 30 shown therein, portion 34 is seen to have ribbed portions 54, 56 and 58, which ribbed portions serve as a restraint, restraining the movement of the ball valve 50 during its movement away from the opening of the feedline 26 during non-operation of the pump 16 of FIG. 1.

Figure 3:
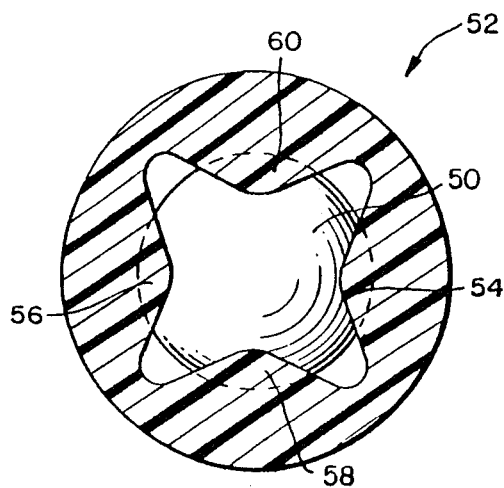
FIG. 3 is a sectional view, taken along line 3—3 in FIG. 2, of the pump-actuated sequencing valve.

FIG. 3 is a sectional view of the portion 34, including the ribbed portions 54, 56 and 58 thereof, as seen along line 3—3 in FIG. 2. In addition, the ball valve 50 is shown by means of a dotted line outline in FIG. 3. Thus, referring to FIG. 3, it can be seen that the dimensions of the ball valve 50 are such that the ball valve 50 is restrained from passing through the opening between the ribbed portions 54, 56, 58 and 60 in FIG. 3.

Of course, other restraining means, for restraining movement of the ball valve 50 of FIG. 2, would be evident to one of skill in the art. For example, instead of utilizing ribbed portions 54, 56, 58 and 60 of FIGS. 2 and 3, one could employ a mesh screen or other device which would restrain the ball valve 50 so as to limit its motion away from the feedline 26 (FIG. 2), while at the same time not impeding the flow of fluid from the feedline 26 through the portion 34 to the portion 36, for eventual flow through feedline 38 to the needle 40 inserted in the vein of the patient.

Figure 4:
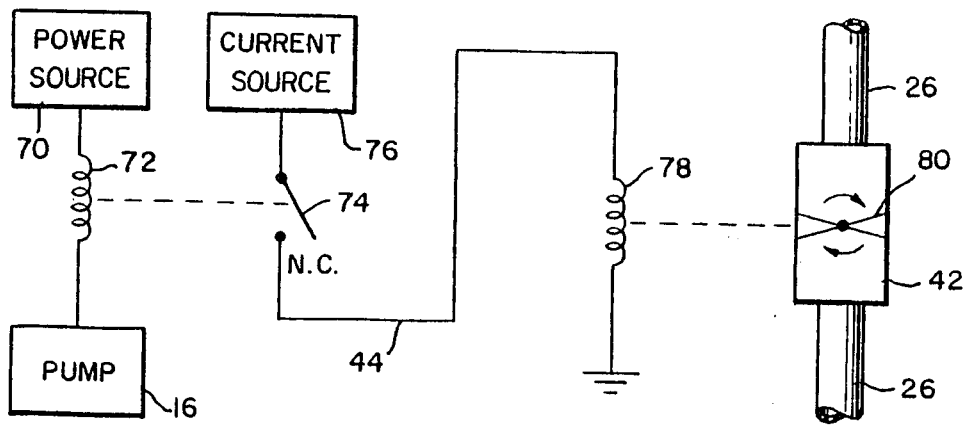
FIG. 4 is a detailed diagram of the arrangement by means of which operation/non-operation of pump 16 (FIG. 1) automatically closes/opens valve 42.

FIG. 4 is a detailed diagram of the arrangement by means of which operation/non-operation of the pump automatically closes/opens the valve 42 of FIG. 1.

Specifically, operation of the pump 16 is achieved by turning on of a power source 70 connected, via solenoid 72, to the pump 16. Since solenoid 72 forms a solenoid/relay switch combination with relay switch 74 (as indicated by the dotted line connecting these two elements in FIG. 4), flow of current through solenoid 72 causes normally closed switch 74 to open. This interrupts flow of current from a current source 76, via line 44, to a solenoid 78. Lack of current flow through solenoid 78 causes a valve mechanism 80 in valve 42 (also shown in FIG. 1 and discussed above) to move to the closed position, as shown in FIG. 4. Thus, flow of saline solution from reservoir 20 (FIG. 1), via feedline 26, to sequencing valve 30 is impeded.

Conversely, when it is desired to stop operation of the pump 16, power source 70 is turned off, and current flow through solenoid 72 ceases. This causes relay switch 74 to assume its normally closed position, and current flows from current source 76, via switch 74 and line 44, to solenoid 78. Current flow through solenoid 78 causes valve mechanism 80 in valve 42 to rotate to the open position (vertical position perpendicular to its position as shown in FIG. 4), and this permits flow of saline solution from reservoir 20, via feedline 26, to sequencing valve 30.

Of course, the arrangement shown in FIG. 4 is merely one arrangement which can be employed to achieve generation of the necessary control signals through line 44 (FIG. 1) in order to automatically open/close valve 42 in response to turning off/turning on of the pump 16.

While preferred forms and arrangements have been shown in illustrating the invention, it is to be clearly understood that various changes in detail and arrangement may be made without departing from the spirit and scope of this disclosure.

What is claimed is:

1. A pump-actuated sequencing system for sequentially administering to a patient two fluids contained in first and second respective reservoirs, wherein fluid is pumped from said first reservoir by means of a pump, said system comprising a pump-actuated sequencing valve, said valve comprising:
    a first portion;
    means for fluidly connecting said first portion to said first reservoir;
    a second portion connected to said first portion; and
    means for fluidly connecting said second portion to said second reservoir;
    said second portion including ball valve means for selectively blocking flow of fluid to and from said second reservoir in response to operation of the pump, and for selectively permitting flow of fluid from said second reservoir in response to non-operation of the pump;
    said valve further comprising a third portion connecting each of said first and second portions to the patient for conveying fluid to the patient;
    said system further comprising a further valve disposed between said second reservoir and said second portion, and control means operatively connecting said pump to said further valve for opening said further valve in response to non-operation of the pump so as to permit flow of fluid from said second reservoir to said second portion.

2. The valve of claim 1, wherein said ball valve means comprises a ball which freely floats within said second portion when said pump is inoperative, and restraining means for restraining movement of said freely floating ball.

3. The valve of claim 2, wherein said second portion comprises a conduit having a surrounding wall, said restraining means comprising built-up portions in said surrounding wall and located between said freely floating ball and said third portion.

4. The system of claim 1, wherein said control means comprises a current source colocated with said pump, a solenoid colocated with said further valve, a control line connecting said current source to said solenoid, and a switch inserted in said control line, and wherein said switch remains normally closed in response to non-operation of said pump so as to permit flow of current from said current source to said solenoid, said solenoid actuating said further valve to an open position in response to reception of said current flow.

5. A pump-actuated sequencing system for sequentially administering to a patient two fluids contained in first and second respective reservoirs, wherein fluid is pumped from said first reservoir by means of a pump, said system comprising a pump-actuated sequencing valve, said valve comprising:
    a first portion;
    means for fluidly connecting said first portion to said first reservoir so as to provide a path for the fluid pumped from said first reservoir to said first portion;
    a second portion connected to said first portion; and
    means for fluidly connecting said second portion to said second reservoir;
    said second portion including ball valve means for selectively blocking flow of fluid to and from said second reservoir in response to operation of the pump, and for selectively permitting flow of fluid from said second reservoir in response to non-operation of the pump;
    said valve further comprising a third portion connecting each of said first and second portions to the patient for conveying fluid to the patient;
    said system further comprising a further valve disposed between said second reservoir and said second portion, and control means operatively connecting said pump to said further valve for closing said further valve in response to operation of said pump so as to impede flow of fluid from said second reservoir to said second portion.

6. The system of claim 5, wherein said control means comprises a current source colocated with said pump, a solenoid colocated with said further valve, a control line connecting said current source to said solenoid, and a switch inserted serially in said control line, and wherein said switch moves to an open position in response to operation of said pump so as to impede flow of current from said current source to said solenoid, said solenoid actuating said further valve to a closed position in response to non-reception of said current flow.

7. A pump-actuated sequencing system for sequentially administering, to a patient, two fluids contained in respective first and second reservoirs, comprising:
    pump means for pumping fluid from said first reservoir;
    first conveying means providing a flow path from said first reservoir to the patient for conveying said fluid pumped by said pump means to the patient;
    second conveying means providing a flow path from said second reservoir to the patient for conveying fluid from said second reservoir to the patient;
    valve means disposed between said second reservoir and the patient for selectively blocking or permitting flow of fluid from said second reservoir to the patient; and
    control means, connecting said pump means to said valve means, for selectively opening said valve means in response to non-operation of said pump means so as to permit flow of fluid from said second reservoir to the patient, and for selectively closing said valve means in response to operation of said pump means so as to impede flow of fluid from said second reservoir to the patient.

8. The system of claim 7, wherein said control means comprises a current source colocated with said pump means, a solenoid colocated with said valve means, a control line connecting said current source to said solenoid, and a switch serially inserted in said control line.

9. The system of claim 8, wherein said switch remains normally closed in response to non-operation of said pump means so as to permit flow of current from said current source to said solenoid, said solenoid actuating said valve means to an open position in response to reception of said current flow.

10. The system of claim 8, wherein said switch moves to a normally open position in response to operation of said pump means so as to impede flow of current from said current source to said solenoid, said solenoid actuating said valve means to a closed position in response to non-reception of said current flow.

* * * * *